(12) United States Patent
Enquist et al.

(10) Patent No.: US 6,484,563 B1
(45) Date of Patent: Nov. 26, 2002

(54) METHOD AT DETECTION OF PRESENCE OF HYDROGEN GAS AND MEASUREMENT OF CONTENT OF HYDROGEN GAS

(75) Inventors: Fredrik Enquist, Linkoping (SE); Peter Hebo, Linkoping (SE)

(73) Assignee: Sensistor Technologies AB, Linkoping (SE)

(*) Notice: Subject to any disclaimer, the term of this patent is extended or adjusted under 35 U.S.C. 154(b) by 0 days.

(21) Appl. No.: 09/893,097

(22) Filed: Jun. 27, 2001

(51) Int. Cl.[7] .................. G01N 27/04; G01N 31/00; G01N 1/22; H01L 29/66
(52) U.S. Cl. ............. 73/31.06; 73/23.31; 73/23.2; 73/1.02; 422/94; 324/71.5
(58) Field of Search ............... 73/31.06, 23.31, 73/23.2, 1.02; 422/98, 90; 324/71.5

(56) References Cited

U.S. PATENT DOCUMENTS

| | | | | |
|---|---|---|---|---|
| 3,960,495 A | * | 6/1976 | Tantram | 23/232 E |
| 4,030,340 A | * | 6/1977 | Chang et al. | 73/23 |
| 4,058,368 A | | 11/1977 | Svensson et al. | 23/254 E |
| 4,072,043 A | * | 2/1978 | Naizer et al. | 73/23 |
| 4,101,282 A | * | 7/1978 | Ririe | 23/254 R |
| 4,316,382 A | * | 2/1982 | Woodruff | 73/27 R |
| 4,348,732 A | * | 9/1982 | Kreft | 364/571 |
| 4,664,868 A | * | 5/1987 | Novack et al. | 422/94 |
| 5,184,500 A | * | 2/1993 | Krema et al. | 73/23.2 |
| 5,223,783 A | * | 6/1993 | Wilis | 324/71.5 |
| 5,325,705 A | * | 7/1994 | Tom | 73/31.03 |
| 5,521,099 A | * | 5/1996 | Glaunsinger et al. | 436/151 |
| 5,608,156 A | * | 3/1997 | Ando et al. | 73/31.06 |
| 5,668,301 A | * | 9/1997 | Hunter | 73/23.2 |

FOREIGN PATENT DOCUMENTS

| | | |
|---|---|---|
| SE | 7411342-4 | 3/1976 |

OTHER PUBLICATIONS

K I. Lundstrom, M. S. Shivaraman, and C. Svensson, A Hydrogen sensitive Pd–gate MOS transistor C', J. Applied Physics., 46, pp. 3876–3881 (1975).

I. Lundstrom, M. S. Shivaraman, and C. Svensson, "Chemical reactions on palladium surfaces studied with Pd–MOS structures", Surface Science, 64, p. 497 (1977).

I. Lundstrom, "Hydrogen sensitive MOS–structures. Part 1: Principles and Applications" Sensors and Actuators, 1, pp. 403–426 (1981).

I. Lundstrom, and D. Soberer, "Hydrogen sensitive MOS–structures. Part 2: Characterisation", Sensors and Actuators, 2, pp. 105–138 (1981/82).

M. Armgarth, C. Nylander, I. Lundstrom, and C. Svensson, "Some physical phenomena observed in Pd gate MOS Hydrogen Sensors"; Linkoping Studies in Science and Technology. Dissertations nr 107, p. 30 ff, Linkoping University, Sweden (1983).

* cited by examiner

*Primary Examiner*—Hezron Williams
*Assistant Examiner*—David J. Wiggins
(74) *Attorney, Agent, or Firm*—Merchant & Gould, P.C.

(57) ABSTRACT

The present invention relates to a method at detection of presence of hydrogen gas and measurement of content of hydrogen gas. The detection is performed by means of a hydrogen gas sensitive semiconductor sensor, whose output signal is used for determination of the content of hydrogen gas in the gas sample. The semiconductor sensor is exposed to the gas sample during a detection interval, which is preceded by a time-interval of preconditioning treatment during which the semiconductor sensor is exposed to a surrounding gas atmosphere. The invention is characterized in that the gas atmosphere contains a negligible amount of oxygen, hydrogen and carbon monoxide compared to the gas sample and that the time interval is many times longer than the detection interval.

5 Claims, 1 Drawing Sheet

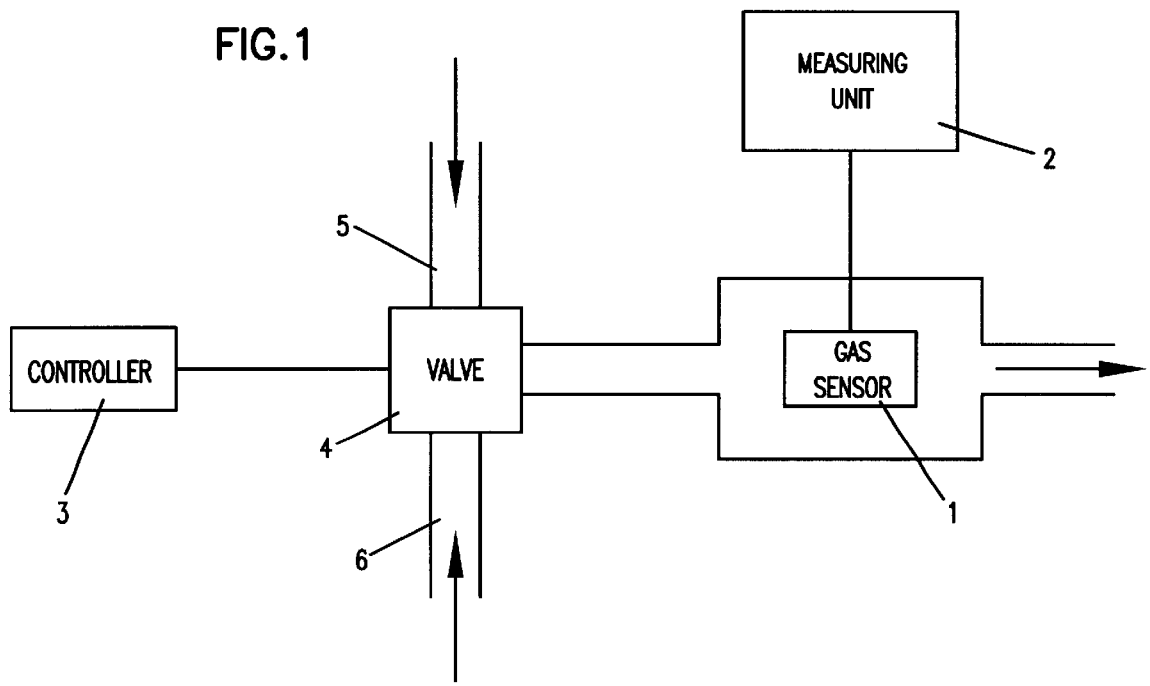

METHOD AT DETECTION OF PRESENCE OF HYDROGEN GAS AND MEASUREMENT OF CONTENT OF HYDROGEN GAS

BACKGROUND OF THE INVENTION

The present invention relates to a method according to the preamble of claim 1.

There are a large number of different methods, which can be used at detection of presence of gases and measurement of gas concentrations. A common factor for these methods is that they generate a value as a measure of the presence or concentration of a gas. At applications when the detection and measurements will be performed continuously or at a number of successive occasions, it is preferred to use a device, a so-called sensor, which transforms the gas concentration into an electric signal.

The sensors known today include all types of sensors from complex technical systems, like for example mass spectrometers and gas chromatographs, to small and relatively simple sensors, like for example sensors measuring the thermal conductivity of a gas. Most of these sensors measure physical or chemical properties of the atoms or molecules of a gas.

Another type of sensor, which instead measures the presence of molecules of a gas is described in SE-7411342-4. This sensor, which is a semiconductor sensor, exhibits advantages, such as very high sensitivity to and selectivity for hydrogen gas, moderate energy consumption, small size and possibility for rational manufacturing. The term "semiconductor sensor" refers herein to the type of sensor described in SE-7411342-4 but includes also other structures of catalytic metals and semiconductors working along the principles described below.

The semiconductor sensor comprises a catalytic metal layer, which captures hydrogen molecules and decomposes these molecules into hydrogen atoms, which diffuse through the metal layer and give rise to an electric signal in the semiconductor structure. The amount of hydrogen atoms within the metal and the amount of hydrogen gas in the surroundings of the metal, equilibrate after a certain time. Thus, the output signal from the semiconductor sensor is dependent of the hydrogen gas concentration in its surroundings. The output signal is also depending on the relationship between the content of oxygen gas and hydrogen gas in the surroundings, which will be described below.

As previously known, the semiconductor sensor provides greater signals for hydrogen gas when the measurements are performed in an environment free of oxygen compared to measurements in an environment containing oxygen. Oxygen in the surroundings of the semiconductor sensor influences the measurements by producing an adsorbed oxygen layer on the metal surface of the semiconductor sensor. The higher the concentration of oxygen gas in the surroundings of the semiconductor sensor, the greater the number of molecules and atoms of oxygen adsorbed on the metal surface. This implies, that the number of sites, which molecules of hydrogen gas can be adsorbed to, is being reduced concurrently with the number of molecules and atoms of oxygen being increased on the metal surface. Furthermore, oxygen reacts with hydrogen adsorbed to the metal surface with a resulting production of water and hydrogen is thereby removed from the metal surface without having influenced the output signal.

Most gas samples subject to analysis regarding hydrogen, contains air and/or oxygen and as it is relatively difficult and complicated to purify gas samples from oxygen in an effective and reproducible way, there has been no practical way to take full advantage of the sensitivity of semiconductor sensors. Purification of gas samples from oxygen also results in that the total analysis time will be considerable lengthened, as this requires an extra step of sample preparation.

Consequently, oxygen is counteracting the sensitivity of the semiconductor sensor for hydrogen gas and influences both the equilibrium signal, i e the output signal when equilibrium between the amount of hydrogen gas in the surroundings and hydrogen within the metal is obtained and the time derivative of the output signal, i e the rate with which the output signal increases at increased hydrogen gas concentration. When interpreting the output signal of the semiconductor sensor, it is previously known to, either use the equilibrium signal or the time derivative of the output signal.

The aforementioned interactions between oxygen and a semiconductor sensor are also valid for carbon monoxide, which also is present in many gas samples.

SUMMARY OF THE INVENTION

The object of the present invention is to provide an increased sensitivity for hydrogen gas of the semiconductor sensor. This is achieved according to the method of the invention by means of the measurements indicated in the characterizing part of claim 1.

BRIEF DESCRIPTION OF THE DRAWING

In the following the invention will be explained in more detail by means of an example of an embodiment of the present invention and with reference to the accompanying drawing.

FIG. 1 illustrates a sensor system for detection and measurement of content of hydrogen gas in a gas sample.

In the drawing designation 1 indicates a semiconductor sensor, to which a measuring instrument 2 is connected. A controller unit 3 controls valve 4, which is connected to the semiconductor sensor 1 and which has an inlet 5 for a gas sample and an inlet 6 for another gas.

DESCRIPTION OF THE INVENTION

At detection and measurement of the content of hydrogen gas in a gas sample, the semiconductor sensor 1 is exposed to a gas sample during a certain detection period. As previously described, the catalytic metal layer of the semiconductor sensor 1 decomposes molecules of hydrogen into atoms of hydrogen, which diffuse through the metal layer and generate an electric signal in the semiconductor sensor 1. The electric signal is measured by the measuring instrument 2.

The valve 4 and the two inlets 5 and 6 are according to the present invention arranged in the sensing system in order to make it possible to supply different gases to the semiconductor sensor 1. The supply of gas to the semiconductor sensor 1 is controlled by the controller unit 3, which controls the position of the valve 4, so that gas may pass from either of the inlets 5 or 6 through the valve 4 to the semiconductor sensor 1. During the detection period the gas sample is supplied through inlet 5 to the semiconductor sensor 1.

According to the present invention there is a preconditioning period before each detection period. The length of the detection period is preferably between 0.01 s and 10 s and the length of the preconditioning period is between 1 s and 1 h and the preconditioning and detection periods may be repeated at regular intervals. The semiconductor sensor 1 is during the preconditioning period kept in an environment free of oxygen and carbon monoxide. Then the controller unit 3 controls the valve 4, so that a gas free of oxygen and carbon monoxide, preferably nitrogen, may pass from inlet 6 through the valve 4 to the semiconductor sensor 1. The exposure of a gas free of oxygen and carbon monoxide aims to remove oxygen and carbon monoxide molecules, which may be adsorbed to the metal surface of the semiconductor sensor 1 and thereby influence the output signal. In order to obtain as high sensitivity as possible the preconditioning period should be so long that a state of equilibrium between the amount of oxygen and carbon monoxide molecules adsorbed on the metal surface of the semiconductor sensor 1 and those present in the surroundings of the semiconductor sensor 1 is obtained, i e such that the metal surface is obtained essentially free of oxygen and carbon monoxide. The highest sensitivity is achieved when the preconditioning period is much longer than the detection period, i e when the relationship preconditioning period/detection period is high. Furthermore the semiconductor sensor is kept in an environment free of oxygen and carbon monoxide before the first measurement.

When the surface layer of the semiconductor sensor 1 is essentially free of oxygen and carbon monoxide, the measurements may be performed on a gas sample including carbon monoxide and/or oxygen, because the detection period is so short that the measurement is terminated before oxygen and carbon monoxide are able to influence the sensitivity of the sensor.

Consequently, the measurement is performed according to the present invention after the exposure of the semiconductor sensor 1 to the gas free of oxygen and carbon monoxide during a detection period. The content of hydrogen gas in the gas sample is determined in the present invention in an actually known way by using the maximum rate by which the output signal from the semiconductor sensor 1 increases, i e the maximum of the time derivative of the output signal.

It is apparent for anyone skilled in the art that the present invention is not restricted to the above described embodiment. For example, argon or helium may be used as the inert gas instead of nitrogen.

We claim:

1. Method of detection of hydrogen gas and measurement of content of hydrogen gas in a gas sample by means of a hydrogen gas sensitive semiconductor sensor, whose output signal is used for determination of the content of hydrogen gas in the gas sample, at which the detection is performed by exposing the semiconductor sensor to the gas sample during a detection period, which is preceded by a preconditioning period during which the semiconductor sensor is exposed to a surrounding gas atmosphere, wherein, that the gas atmosphere contains negligible amounts of oxygen and carbon monoxide compared to the gas sample and that the highest sensitivity of the semiconductor sensor is achieved when the preconditioning period is considerably longer than the detection period.

2. Method according to claim 1, wherein, that the length of the detection period is between 0.01 s and 10 s.

3. Method according to claim 1, wherein, that the length of the preconditioning period is between 1 s and 1 h.

4. Method according to claim 1 for measurement of the content of hydrogen gas in the gas sample, wherein, that the maximum value of the time derivative of the output signal is used for determination of the content of hydrogen gas in the gas sample.

5. Method according to claim 1, wherein, that the gas atmosphere consists of an inert gas, preferably nitrogen.

* * * * *

UNITED STATES PATENT AND TRADEMARK OFFICE
CERTIFICATE OF CORRECTION

PATENT NO.    : 6,484,563 B1
DATED         : November 26, 2002
INVENTOR(S)   : Fredrik Enquist et al.

It is certified that error appears in the above-identified patent and that said Letters Patent is hereby corrected as shown below:

<u>Title page,</u>
Item [56], References Cited, insert:

--        U.S. PATENT DOCUMENTS,
6,160,278        December 12, 2000        Liu et al.

FOREIGN PATENT DOCUMENTS
DE 196 38 709 A1    April 9, 1998        Germany
DE 100 08 829 A1    September 6, 2001    Germany
WO    01/54171      July 26, 2001        WIPO --

Signed and Sealed this

Eighteenth Day of March, 2003

JAMES E. ROGAN
*Director of the United States Patent and Trademark Office*